(12) United States Patent
Adams et al.

(10) Patent No.: US 7,455,679 B2
(45) Date of Patent: Nov. 25, 2008

(54) SURGICAL ELONGATE BLADE ASSEMBLY WITH INTERCHANGEABLE INNER MEMBER, KIT AND METHOD RELATING THERETO

(75) Inventors: Kenneth M. Adams, Jacksonville, FL (US); Gary Peters, Knoxville, TN (US)

(73) Assignee: Medtronic Xomed, Inc., Jacksonville, FL (US)

( * ) Notice: Subject to any disclaimer, the term of this patent is extended or adjusted under 35 U.S.C. 154(b) by 850 days.

(21) Appl. No.: 10/781,852

(22) Filed: Feb. 20, 2004

(65) Prior Publication Data

US 2004/0181250 A1    Sep. 16, 2004

Related U.S. Application Data

(60) Provisional application No. 60/448,773, filed on Feb. 20, 2003.

(51) Int. Cl.
*A61B 17/22* (2006.01)
(52) U.S. Cl. .................................................. 606/170
(58) Field of Classification Search .............. 606/167, 606/170, 159, 174, 180; 604/22, 33
See application file for complete search history.

(56) References Cited

U.S. PATENT DOCUMENTS

| 4,705,038 | A | | 11/1987 | Sjostrom et al. |
|---|---|---|---|---|
| 5,152,744 | A | * | 10/1992 | Krause et al. .................. 604/22 |
| 5,601,586 | A | | 2/1997 | Fucci et al. |
| 5,690,660 | A | | 11/1997 | Kauker et al. |
| 5,741,286 | A | * | 4/1998 | Recuset ...................... 606/170 |
| 5,741,287 | A | | 4/1998 | Alden et al. |
| 5,766,200 | A | | 6/1998 | Mazurek et al. |
| 5,857,995 | A | | 1/1999 | Thomas et al. |
| 5,910,152 | A | | 6/1999 | Bays |
| 5,922,003 | A | | 7/1999 | Anctil |
| 5,961,532 | A | | 10/1999 | Finley et al. |
| 6,007,556 | A | | 12/1999 | Kablik et al. |
| 6,533,749 | B1 | | 3/2003 | Mitusina et al. |

FOREIGN PATENT DOCUMENTS

| WO | WO81/01363 | 5/1981 |
|---|---|---|
| WO | WO97/37600 | 10/1997 |

* cited by examiner

*Primary Examiner*—Kevin T Truong

(57) ABSTRACT

A surgical elongate blade assembly with an interchangeable inner member such that the interchangeable inner member can be removed from a tubular outer member and inserted into another tubular outer member having a different configuration during a surgical procedure. The outer members and inner members can be provided as a kit. In one embodiment the outer member has a distal end and a tubular wall with the inner diameter of the tubular wall being greater than the inner diameter of the distal end.

7 Claims, 4 Drawing Sheets

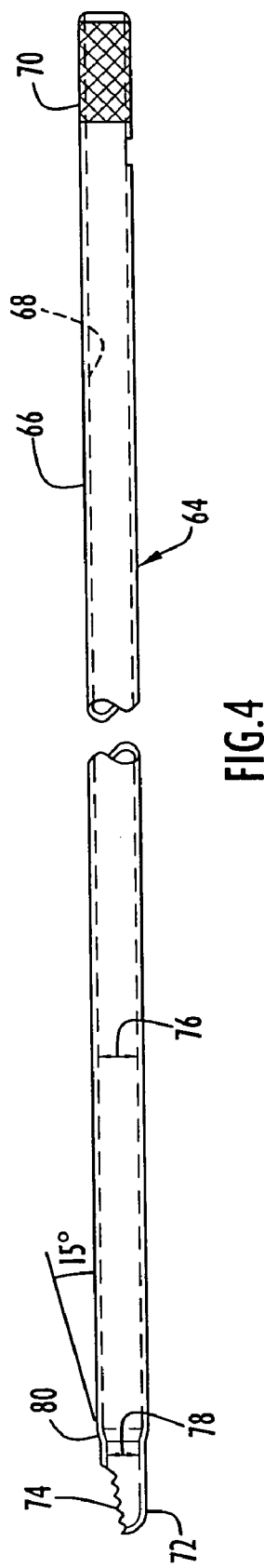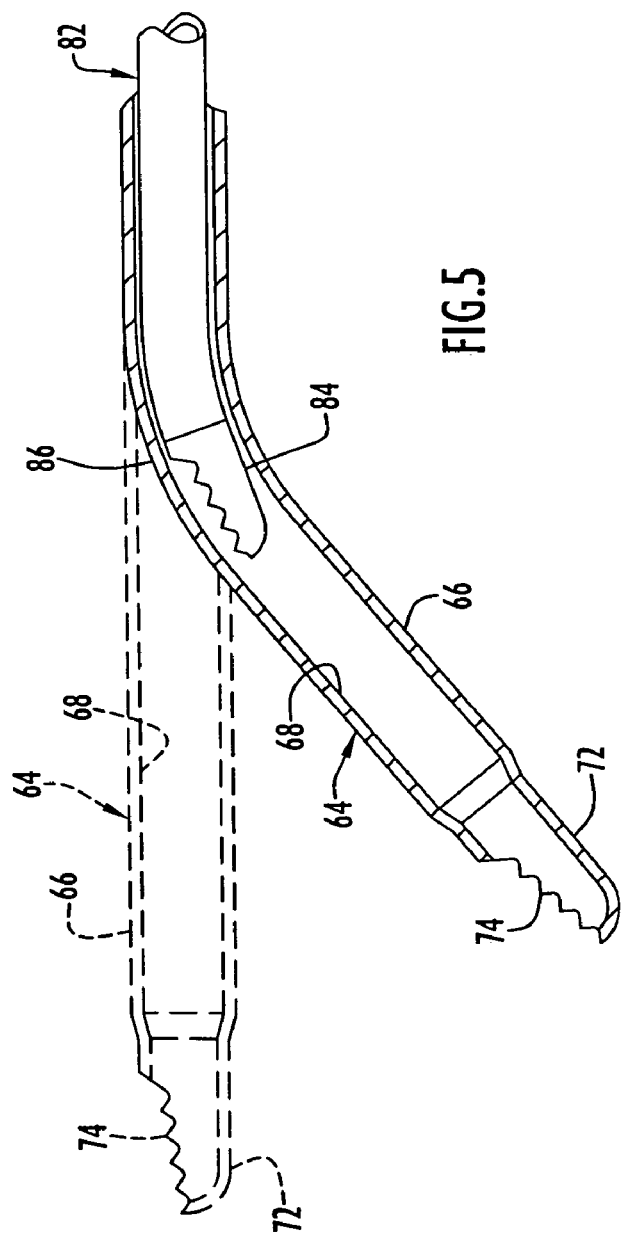

SURGICAL ELONGATE BLADE ASSEMBLY WITH INTERCHANGEABLE INNER MEMBER, KIT AND METHOD RELATING THERETO

CROSS REFERENCE TO RELATED PATENT APPLICATION

This application claims priority from prior provisional patent application Ser. No. 60/448,773 filed Feb. 20, 2003, the entire disclosure of which is incorporated herein by reference.

BACKGROUND OF THE INVENTION

1. Field of the Invention

The present invention relates to elongate blade assemblies for performing surgical procedures on patients and, more particularly, to such blade assemblies formed of outer tubular members and inner members rotatably disposed in the outer members with cutting tips positioned adjacent openings at the distal ends of the outer members.

2. Brief Discussion of the Related Art

Powered elongate blade assemblies are conventionally used in many surgical procedures and typically include a tubular outer member having an opening or window at a distal end thereof and an inner member having a tissue treating distal end, or cutting tip, disposed adjacent the opening in the distal end of the outer member, the inner member being movable, normally rotatably or in an oscillating manner, via a handpiece mounting proximal ends of the inner and outer members. Examples of such powered elongate blade assemblies and systems include the XPS Systems marketed by Medtronic Xomed, Inc. of Jacksonville, Fla. which utilize a STRAIGHTSHOT or STRAIGHTSHOT MAGNUM handpiece for powering the blade assemblies. The blade assemblies can be straight or, for many procedures, have bends therein such that a portion of the elongate blade assembly is angled away from a longitudinal axis passing through the proximal end thereof. In order to accommodate bends in the outer member, the inner member is typically manufactured to be flexible, particularly at the bend area of the outer tubular member. During manufacture, the flexible inner member is normally inserted into a straight outer member; and, thereafter, the outer member is bent with the inner member in place. After such bending, the inner member cannot be withdrawn from the outer member because of the very small clearance between the outer diameter of the cutting tip and the inner diameter of the outer member. During any particular surgical procedure, the surgeon may require a large variety of elongate blade assemblies such that desired angled blade assemblies, windows and cutting tips can be utilized. Additionally, the opening or window at the distal end of the outer member can have various angular orientations as well as configurations of teeth therearound to be selected by the surgeon dependent upon the surgeon's preferences and the specific tissue to be treated or cut. Linvatec Corporation of Largo, Fla. supplies straight blade assemblies to surgeons and a tool for bending the straight blades allowing intraoperative angling of the elongate blade assemblies.

SUMMARY OF THE INVENTION

In accordance with the present invention, a plurality of elongate outer tubular members are provided and each can receive an interchangeable elongate inner member, the outer members being supplied in a variety of distal end and longitudinal configurations including, for example, straight outer members (not bent or angled), outer members angled, or bent, at a distal portion adjacent the distal end, outer members having bent or angled proximal portions and outer members having a combination of angled distal and proximal portions, the outer members being designed to facilitate insertion and removal of the inner member (interchangeability). When the outer members are bent, each has a section proximal of the distal end that is sufficiently larger in diameter than the cutting tip of the inner member to allow the interchangeable inner member to be inserted or removed. In this manner the cost of multiple elongate blade assemblies is reduced by providing a kit or set of a plurality of outer members having different configurations with a single interchangeable inner member or multiple interchangeable inner members, a particular outer member being capable of assembly with a particular inner member depending on tissue and cartilage to be excised and specific anatomical locations to be reached.

In one aspect, the present invention contemplates a method of performing a surgical procedure on a patient including the steps of treating tissue of the patient with an elongate blade assembly including a first elongate outer tubular member via a cutting tip of an inner member rotatable within the outer member, removing the inner member from the first outer member, inserting the inner member in a second elongate outer tubular member having a configuration different from the configuration of the first outer member and treating tissue of the patient via the cutting tip of the inner member.

The present invention can also be characterized in a kit for use in performing a surgical procedure with an elongate blade assembly including at least two elongate outer tubular members each having a different configuration and an interchangeable elongate inner member insertable in and removable from each of the outer members. The different configurations can relate to longitudinal configurations such as bends, or distal end configurations, such as distal end opening design or orientation.

The present invention is additionally characterized in an elongate outer tubular member for use in an elongate blade assembly having a rotatable inner member to be received in the outer member, the outer member being formed by a tubular wall having an inner diameter greater along a bent portion of the outer member than the inner diameter at the distal end of the outer member to facilitate passage of the cutting tip of the inner member during insertion in and removal from the outer member.

Other aspects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 4 is a broken side view of an outer tubular member, prior to bending, in accordance with the present invention.

FIG. 5 is a broken side view, partially in section of the outer tubular member of FIG. 4 with an inner member passing therethrough in accordance with the present invention.

DESCRIPTION OF THE PREFERRED EMBODIMENTS

Figure 1:
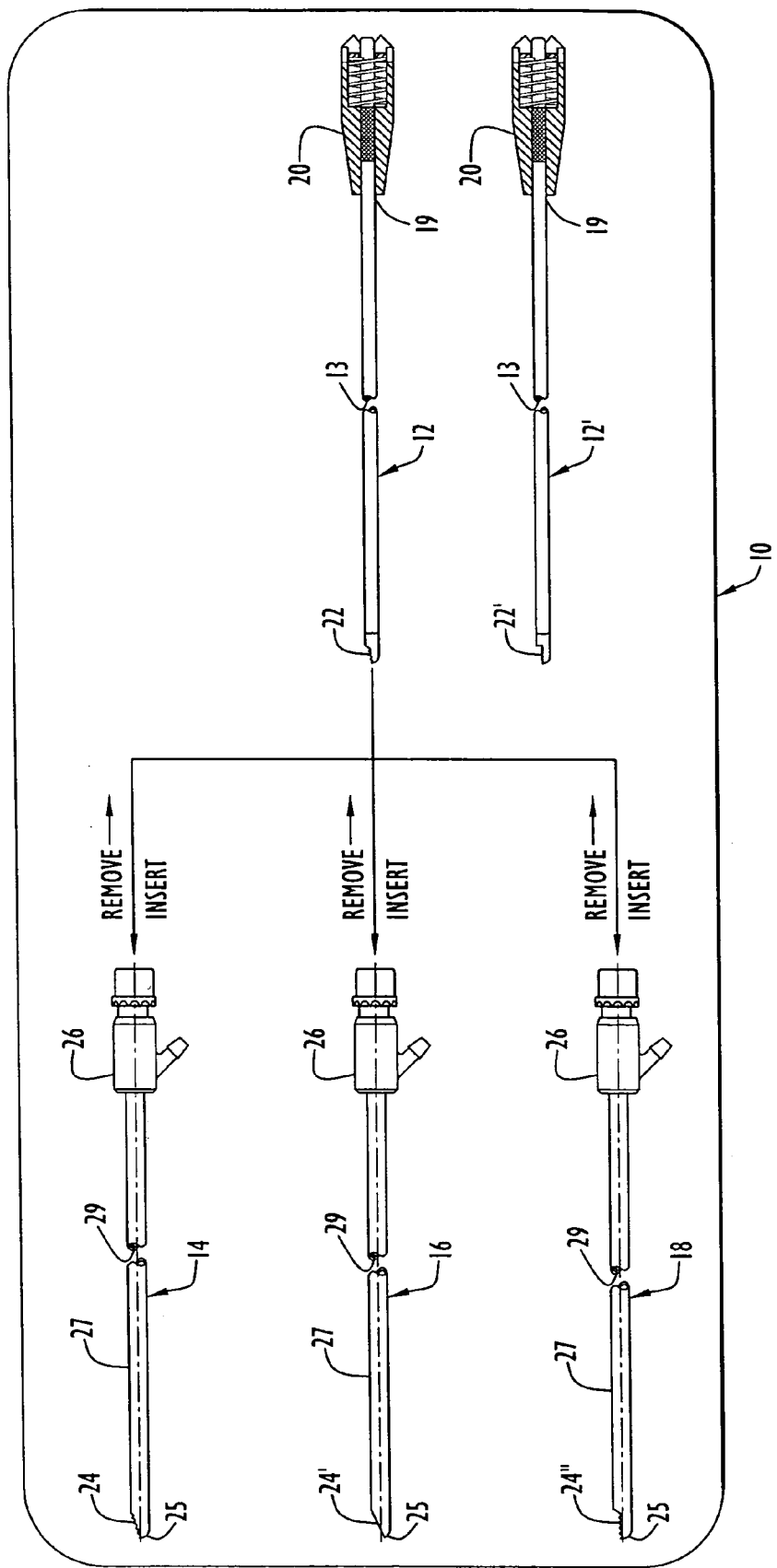
FIG. 1 is a broken plan view of an elongate blade assembly surgical procedure kit or set including interchangeable inner members and straight outer members according to the present invention.

An exemplary elongate blade assembly surgical procedure kit or set 10 in accordance with the present invention is shown in FIG. 1. A prior art elongate blade assembly is shown in FIG. 20 of U.S. Pat. No. 5,910,152 to Bays et al, the disclosure of which is incorporated herein by reference. An elongate blade assembly of the type shown in U.S. Pat. No. 5,910,152 is formed, in accordance with the present invention, by insertion of an interchangeable elongate inner member 12 in any of a plurality of elongate tubular outer members 14, 16 or 18. Inner member 12 can be tubular with a lumen 13 such that cut tissue can be aspirated therethrough and has a proximal end 19 carrying a hub 20 adapted to be driven rotatably, including oscillation, by a handpiece, such as shown in U.S. Pat. No. 5,910,152, within the outer member with which it is assembled. The inner member 12 terminates distally at a tissue treating distal end, or cutting tip, 22 positioned adjacent an opening or window 24, 24' or 24" in the distal ends 25 of the outer members after assembly. Cutting tip 22 can have any desired configuration, such as the toothed or serrated configuration shown. Each outer member has a proximal end 26 adapted to be mounted on the handpiece. The outer members 14, 16 and 18 differ in configuration primarily only in the configuration of the distal end openings, each having a different peripheral edge for use with different tissue. For example, outer member 14 has an angled toothed design (Medtronic Xomed, Inc. TRI-CUT); outer member 16 has a smooth design (Medtronic Xomed, Inc. Serrated Blade); and, outer member 18 has a longitudinal toothed design (Medtronic Xomed, Inc. SHARK). Each of the outer members 14, 16 and 18 has a tubular wall 27 running substantially the length thereof to define a lumen 29 for receiving the inner member and has a straight longitudinal configuration such that inner member 12 can be either rigid or flexible. As well as having different distal end openings, outer members 14, 16 and 18 can also have opening positions in different orientation, i.e. up, down, left, right. The kit 10 could also have a plurality of inner members 12 having cutting tips different from cutting tips 22 such as inner member 12' having a shaver-type cutting tip 22'. The various inner members can be interchanged with the various outer members as desired. Since the outer members 14, 16 and 18 have straight configurations, their lumens 29 can have a constant inner diameter therealong only slightly greater than the outer diameter of the inner member cutting tips to permit the cutting tips to properly and stably rotate in the distal ends of the outer members and to permit the inner members to be interchanged, i.e. inserted and removed, with the outer members.

Figure 2:
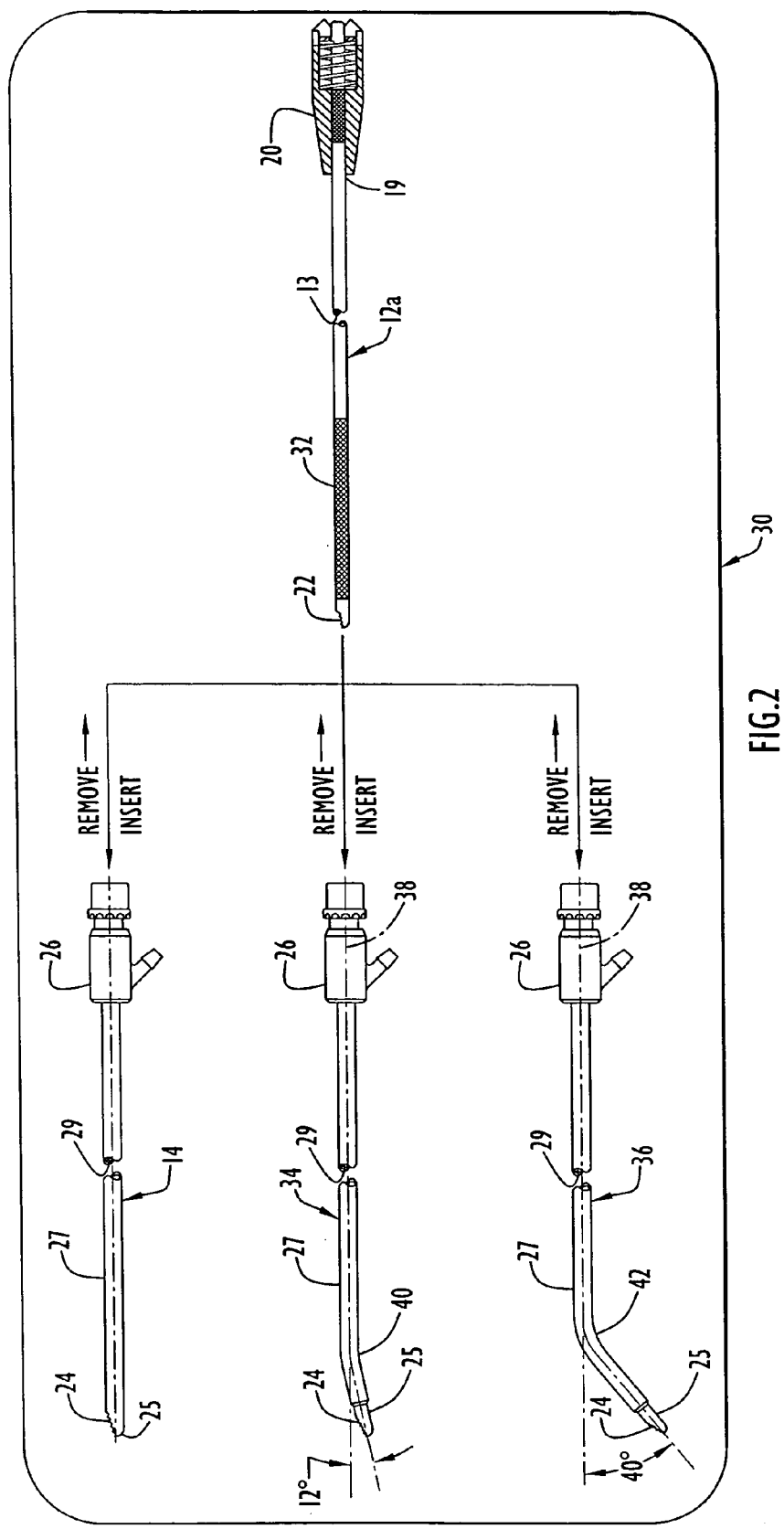
FIGS. 2 and 3 are broken plan views of elongate blade assembly surgical procedure kits or sets including interchangeable inner members and straight and angled outer members according to the present invention.

Another kit or set 30 is shown in FIG. 2 and includes an inner member 12a having the same general overall configuration as inner member 12 of FIG. 1 with the exception that the portion of the inner member adjacent the cutting tip 22 is constructed so as to be flexible as shown at 32. The flexible portion 32 can be made in any suitable manner, for example, as shown in U.S. Pat. No. 5,922,003 to Anctil et al and in U.S. Pat. No. 6,533,749 to Mitusina et al, both assigned to the assignee of the present application and incorporated herein by reference. Illustrated in FIG. 2 are a straight outer member 14, as also shown in FIG. 1, and angled or bent outer members 34 and 36. A longitudinal axis 38 extends through the proximal ends of outer members 34 and 36. Outer member 34 has a bent portion 40 adjacent distal end 25 extending angularly away from the longitudinal axis 38 at an angle of 12°. Outer member 36 has a bent portion 42 adjacent distal end 25 extending angularly away from longitudinal axis 38 at an angle of 40°.

When the inner member 12a is assembled with or inserted in either of outer members 34 or 36, flexible portion 32 will be aligned with bent portions 40 or 42 to allow the inner member to pass through the bent portion such that the cutting tip 22 of the inner member is positioned adjacent the opening 24 in the distal end 25 of the outer member. The distal end 25 of each of bent outer members 34 and 36 has an inner diameter less than the inner diameter of the tubular walls 27 forming lumen 29 in the outer members. The inner diameter at the distal ends 35 is of close tolerance with the outer diameter of the cutting tip 22 whereas the inner diameter at the bent portion is sufficiently greater than the outer diameter of the cutting tip 22 to allow passage of the cutting therethrough to facilitate insertion and removal of the inner member.

Figure 3:
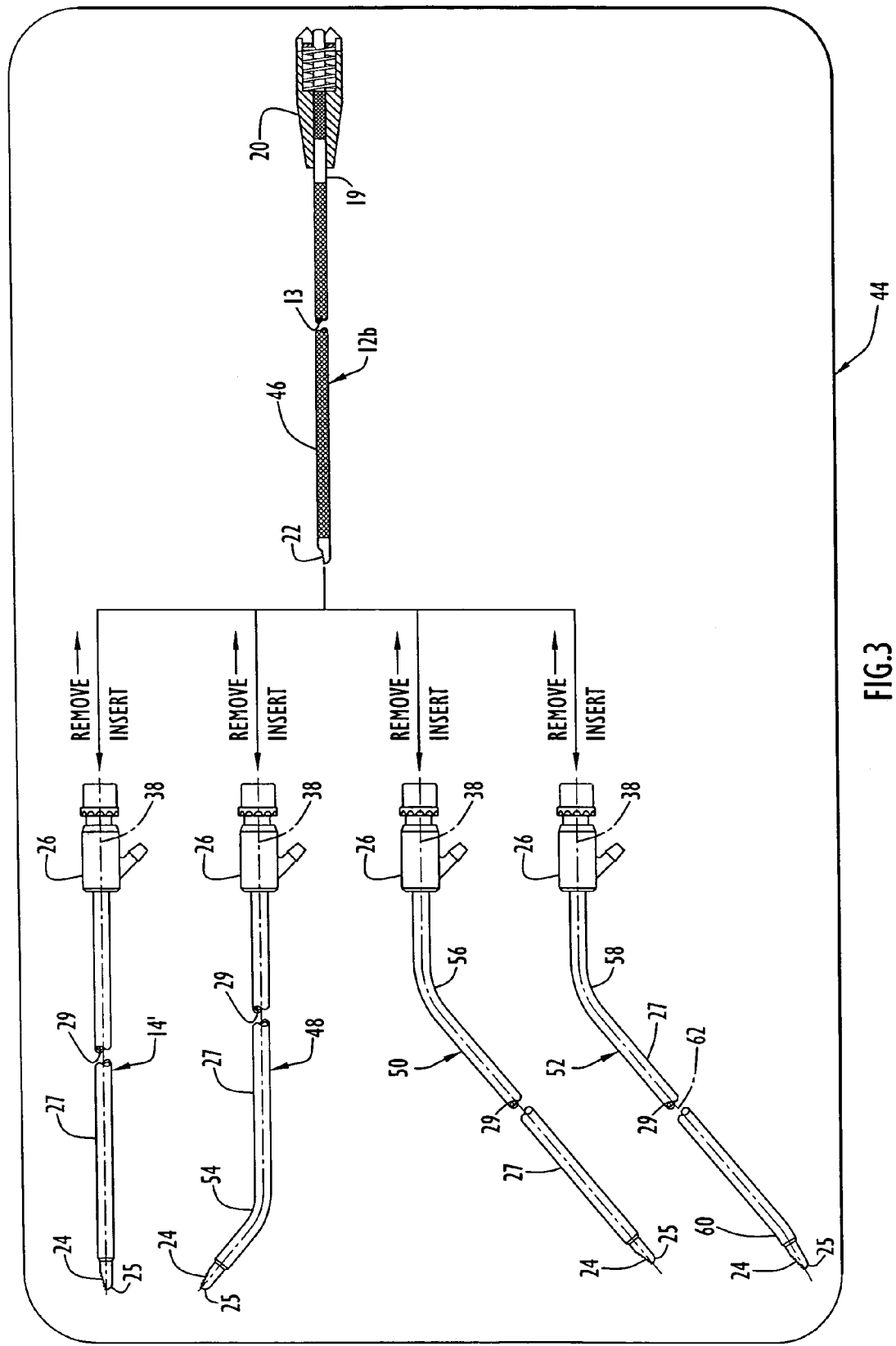

Another kit or set 44 is shown in FIG. 3 and includes an inner member 12b having the same general overall configuration as inner member 12 of FIG. 1 and inner member 12a of FIG. 2 with the exception that the inner member is constructed so as to be flexible along the length thereof as shown at 46. The flexible construction can be made in any suitable manner as described above with respect to FIG. 2. Illustrated in FIG. 3 are a straight outer member 14N substantially the same as shown in FIG. 1 and angled or bent outer members 48, 50 and 52. A longitudinal axis 38 extends through the proximal ends 26 of the outer members. Outer member 48 has a bent portion 54 adjacent distal end 25 extending angularly away from the longitudinal axis 38. Outer member 50 has a bent portion 56 adjacent proximal end 26 extending angularly away from the longitudinal axis 38. Outer member 52 has two bent portions, a bent portion 58 adjacent the proximal end of the outer member and a bent portion 60 adjacent distal end 25. The bent portion 58 extends angularly away from longitudinal axis 38, and the bent portion 60 extends angularly away from a longitudinal axis 62 of the tubular wall 27 forming the outer member 52 and extending between bent portions 58 and 60. When the inner member 12b is assembled with or inserted in either of outer members 48, 50 or 52, the flexible portion 46 will accommodate the bent portions to allow the inner member to pass through the bent portions such that the cutting tip 22 of the inner member is positioned adjacent the opening 24 in the distal end of the outer member. The distal end of each of the outer members has an inner diameter less than the inner diameter of the tubular wall forming the outer members with the inner diameter at the distal end being of close tolerance with the outer diameter of the cutting tip 22 whereas the inner diameter of the tubular wall at the bent portions is sufficiently greater than the outer diameter of the cutting tip 22 to allow passage of the cutting tip thereby to facilitate insertion and removal of the interchangeable inner member.

To facilitate interchangeability of the inner member, the outer member is designed with a section proximal to the distal end having an inner diameter greater than the inner diameter of the distal end of the outer member and sufficiently greater than the outer diameter of the cutting tip of the inner member. As shown in FIG. 4, an outer member 64 is formed of a tubular wall 66 defining a lumen 68 and extending from a proximal end 70 to a distal end 72 in accordance with the present invention having a window or opening 74 therein. The tubular wall has an inner diameter 76 greater than the inner diameter 78 of the distal end 72. The distal end 72 can be formed by swaging the tubular wall 66 to form a shoulder or chamfer 80 at an angle (e.g. 15°) and provide unitary construction or the distal end can be separately formed and secured to the tubular wall in any suitable manner, such as by welding. FIG. 5 shows outer member 64 in a straight longitudinal configuration in dashed lines and in a bent or angled longitudinal configuration in solid lines with an inner member 82 in the process of passing through lumen 68 with a cutting tip 84 positioned at a bent portion 86. As will be appreciated, due to the increased inner diameter of tubular wall 66 relative to the outer diameter of cutting tip 84 and the inner diameter of distal end 72, movement of the inner member through the outer member is facilitated.

The outer members can have a variety of forms and configurations including straight, various angled distal portions, various angled proximal portions, various angled orientations of the distal openings or windows, various opening or window configurations and various combinations of the above. Accordingly, surgery specific kits or sets can be provided with a single interchangeable inner member or multiple interchangeable inner members and a plurality of outer members and, thus, without the cost of an inner member for each outer member. Reference is made to U.S. Pat. No. 5,910,152 for a detailed disclosure of an exemplary handpiece for mounting or fixing the outer member while also securing and rotatably driving the inner member, the rotational speed and direction being controlled by a motor controller circuit connected to the handpiece.

A typical surgical kit or set for head and neck surgical procedures would include, for example, outer members for sinus surgery, tonsillectomy, tonsillotomy, adenoidectomy and laryngectomy. Kits or sets could also be provided for arthroscopic surgery of the knee, ankle, shoulder or jaw or other minimally invasive procedures.

The cutting tip of the inner member has the same dimensions as used with a straight outer member; however, the bent portion of the outer member will be increased in diameter. For example, a 4 mm outer diameter outer member will accommodate an inner member cutting tip having an outer diameter of 0.1321/0.1334 inch; however, the inner diameter of the tubular wall of the outer member would be increased, in accordance with the present invention, to 0.152/0.154 inch providing a total clearance range of 0.0186/0.0219 inch to facilitate passage of the cutting tip and also allowing greater cord lengths through the bend area. Accordingly, a cutting tip having a length of 0.254 inch will pass through the bend area.

In accordance with the present invention, a method of performing a surgical procedure on a patient involves treating tissue of the patient, such as cutting or shaping the tissue, with an elongate blade assembly formed of an interchangeable inner member assembled with a first outer member and, thereafter, removing the inner member from the first outer member, inserting the inner member in a second elongate outer tubular member having a configuration different from the first outer member and treating tissue with the inner member assembled with the second outer member. The term, "surgical procedure" as used herein relates to an entire procedure which may involve more than one act of surgery, it being important that the interchangeable inner member is utilized only with a single patient unless the elongate blade assembly is sterilized prior to a second use.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of performing a surgical procedure on a patient comprising the steps of treating tissue of the patient with an elongate blade assembly formed of a first elongate outer tubular member having a first configuration and a distal end with an opening therein and an inner elongate member rotatably disposed in the first outer member and having a cutting tip disposed adjacent the opening in the distal end of the first outer member, the outer and inner members having proximal ends removably attached to a handpiece that rotates the inner member within the first outer member to cause the cutting tip of the inner member to contact and treat tissue at the opening in the distal end of the first outer member;

detaching the blade assembly from the handpiece and removing the inner member from the first outer member during the surgical procedure on the patient;

inserting the inner member in a second elongate outer tubular member having a second configuration different from the first configuration and a distal end with an opening therein such that the cutting tip of the inner member is disposed adjacent the opening in the distal end of the second outer member;

attaching the proximal ends of the inner member and the second outer member to the handpiece; and continuing to treat tissue of the patient during the surgical procedure by rotating the inner member within the second outer member and contacting the tissue with the cutting tip of the inner member at the opening in the distal end of the second outer member.

2. A method of performing a surgical procedure as recited in claim 1 wherein the first outer member has a first longitudinal configuration and the second outer member has a second longitudinal configuration different from the first longitudinal configuration.

3. A method of performing a surgical procedure as recited in claim 2 wherein one of the first or second longitudinal configurations is a straight longitudinal configuration, and the other of the first or second longitudinal configurations is an angled longitudinal configuration.

4. A method of performing a surgical procedure as recited in claim 2 wherein one of the first or second longitudinal configurations is an angled longitudinal configuration, and the other of the first or second longitudinal configurations is a different angled longitudinal configuration.

5. A method of performing a surgical procedure as recited in claim 1 wherein the first outer member has a first distal end configuration and the second outer member has a second distal end configuration different from the first distal end configuration.

6. A method of performing a surgical procedure as recited in claim 5 wherein the first and second distal end configurations are different from one another in the configuration of the openings at the distal ends of the first and second outer members.

7. A method of performing a surgical procedure as recited in claim 5 wherein the first and second outer members having cutting edges adjacent the openings at the distal ends of the first and second outer members, and the first and second distal end configurations are different from one another in the configuration of the cutting edges.

* * * * *